US010617400B2

(12) United States Patent
Enoki et al.

(10) Patent No.: US 10,617,400 B2
(45) Date of Patent: Apr. 14, 2020

(54) CONTROL DEVICE, CONTROL METHOD, PROGRAM, AND SOUND OUTPUT SYSTEM

(71) Applicant: SONY CORPORATION, Tokyo (JP)

(72) Inventors: Junichiro Enoki, Kanagawa (JP); Yasuaki Takahashi, Kanagawa (JP); Seiji Wada, Kanagawa (JP); Koji Kashima, Kanagawa (JP); Kenta Yamaguchi, Kanagawa (JP); Yukihiro Nakamura, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/091,179

(22) PCT Filed: Jan. 24, 2017

(86) PCT No.: PCT/JP2017/002196
§ 371 (c)(1),
(2) Date: Oct. 4, 2018

(87) PCT Pub. No.: WO2017/187676
PCT Pub. Date: Nov. 2, 2017

(65) Prior Publication Data
US 2019/0125319 A1      May 2, 2019

(30) Foreign Application Priority Data
Apr. 28, 2016   (JP) .................................. 2016-090417

(51) Int. Cl.
*A61B 17/00*      (2006.01)
*A61B 90/00*      (2016.01)
(Continued)

(52) U.S. Cl.
CPC .............. *A61B 17/00* (2013.01); *A61B 34/25* (2016.02); *A61B 90/00* (2016.02);
(Continued)

(58) Field of Classification Search
CPC ......... A61B 17/00; A61B 34/25; A61B 90/00; A61B 2034/2055; A61B 2034/2063; A61B 2017/00084; A61B 2017/00115; A61B 2017/00199; A61B 2017/00203; A61B 2017/00221
USPC ........................ 381/55, 56, 58, 110, 111, 124
See application file for complete search history.

(56) References Cited

U.S. PATENT DOCUMENTS

2005/0086056 A1*   4/2005   Yoda ...................... G10L 15/24
                                                               704/246
2006/0052684 A1    3/2006   Takahashi et al.
(Continued)

FOREIGN PATENT DOCUMENTS

JP          11-85876 A        3/1999
JP          2006-211156 A     8/2006
(Continued)

OTHER PUBLICATIONS

International Search Report dated Mar. 21, 2017, in PCT/JP2017/002196, filed Jan. 24, 2017.

*Primary Examiner* — William A Jerez Lora
(74) *Attorney, Agent, or Firm* — Xsensus LLP

(57) ABSTRACT

It is desired that a technique be provided that is capable of ensuring more reliable voice communication during surgery among surgical participants.
Provided is a control device including a sound-output-control unit that controls sound output by a sound-output device on a basis of information related to surgery.

19 Claims, 9 Drawing Sheets

(51) Int. Cl.
*A61B 34/00* (2016.01)
*A61B 34/20* (2016.01)

(52) U.S. Cl.
CPC .......... *A61B 2017/00084* (2013.01); *A61B 2017/00115* (2013.01); *A61B 2017/00199* (2013.01); *A61B 2017/00203* (2013.01); *A61B 2017/00221* (2013.01); *A61B 2034/2055* (2016.02); *A61B 2034/2063* (2016.02)

(56) References Cited

U.S. PATENT DOCUMENTS

| | | | |
|---|---|---|---|
| 2006/0142739 A1* | 6/2006 | DiSilestro | A61B 90/90 606/1 |
| 2015/0092958 A1* | 4/2015 | Van Tol | H04R 27/00 381/92 |
| 2015/0253979 A1* | 9/2015 | Popescu | G06F 3/0304 715/771 |
| 2015/0279368 A1* | 10/2015 | Contolini | G10L 15/08 704/246 |
| 2016/0125882 A1* | 5/2016 | Contolini | H04R 1/08 704/231 |
| 2017/0194008 A1* | 7/2017 | Vandroux | G10L 15/22 |
| 2019/0090954 A1* | 3/2019 | Kotian | G06N 20/00 |

FOREIGN PATENT DOCUMENTS

| | | |
|---|---|---|
| JP | 2015-167863 A | 9/2015 |
| WO | WO 03/094768 A1 | 11/2003 |

\* cited by examiner

| MICROPHONE ID | MICROPHONE POSITION |
|---|---|
| M1 | (X21, Y21) |
| M2 | (X22, Y22) |
| M3 | (X23, Y23) |
| M4 | (X24, Y24) |
| M5 | (X25, Y25) |
| M6 | (X26, Y26) |

| SURGICAL PARTICIPANT | SOUND-OUTPUT DEVICE |
|---|---|
| SURGEON | DIRECTIONAL SPEAKER |
| ANESTHESIOLOGIST | DIRECTIONAL SPEAKER |
| ASSISTANT | DIRECTIONAL SPEAKER |
| CIRCULATING NURSE | EARPHONE |
| SCRUB NURSE | DIRECTIONAL SPEAKER |
| ENDOSCOPIST | DIRECTIONAL SPEAKER |

(0 MIN. AGO) VOICE RECOGNITION RESULTS   (SURGEON)
(1 MIN. AGO) WHAT IS THE BLOOD PRESSURE?   (SURGEON)
(5 MIN. AGO) ...

CONTROL DEVICE, CONTROL METHOD, PROGRAM, AND SOUND OUTPUT SYSTEM

TECHNICAL FIELD

The present disclosure relates to a control device, a control method, a program and a sound output system.

BACKGROUND ART

In recent years, various techniques have been disclosed as techniques for facilitating surgery. For example, a technique is disclosed (for example, refer to Patent Literature 1) in which equipment is correlated beforehand with each of a plurality of surgery types, a plurality of surgery types are displayed as candidates for surgery types, and when a user selects a surgery type from the candidates of types, the equipment correlated with the selected surgery type is presented to the user. With this technique, it is possible to grasp an understanding of the equipment used for the selected surgery type.

CITATION LIST

Patent Literature

Patent Literature 1: JP H11-085876A

DISCLOSURE OF INVENTION

Technical Problem

During surgery it is common for voice communication to be performed among surgical participants. However, there may exist factors that interfere with voice communication. Therefore, it is desired that a technique be provided that is capable of ensuring more reliable voice communication during surgery among surgical participants.

Solution to Problem

According to the present disclosure, there is provided a control device including a sound-output-control unit that controls sound output by a sound-output device on a basis of information related to surgery.

According to the present disclosure, there is provided a control method including controlling, by a processor, sound output by a sound-output device on a basis of information related to surgery.

According to the present disclosure, there is provided a program for causing a computer to function as a control device including a sound-output-control unit that controls sound output by a sound-output device on a basis of information related to surgery.

According to the present disclosure, there is provided a sound-output system including: a sound-output device that performs sound output; and a control device including a sound-output-control unit that controls sound output by the sound-output device on a basis of information related to surgery.

Advantageous Effects of Invention

As described above, according to the present disclosure, a technique is provided that is capable of ensuring more reliable voice communication during surgery among surgical participants. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 7 is a diagram illustrating an example of a configuration of a microphone-arrangement database.

FIG. 8 is a diagram illustrating an example of a configuration of a sound-output-device database.

FIG. 11 is a diagram illustrating an example of a display of voice-recognition results.

MODES FOR CARRYING OUT THE INVENTION

Figure 1:
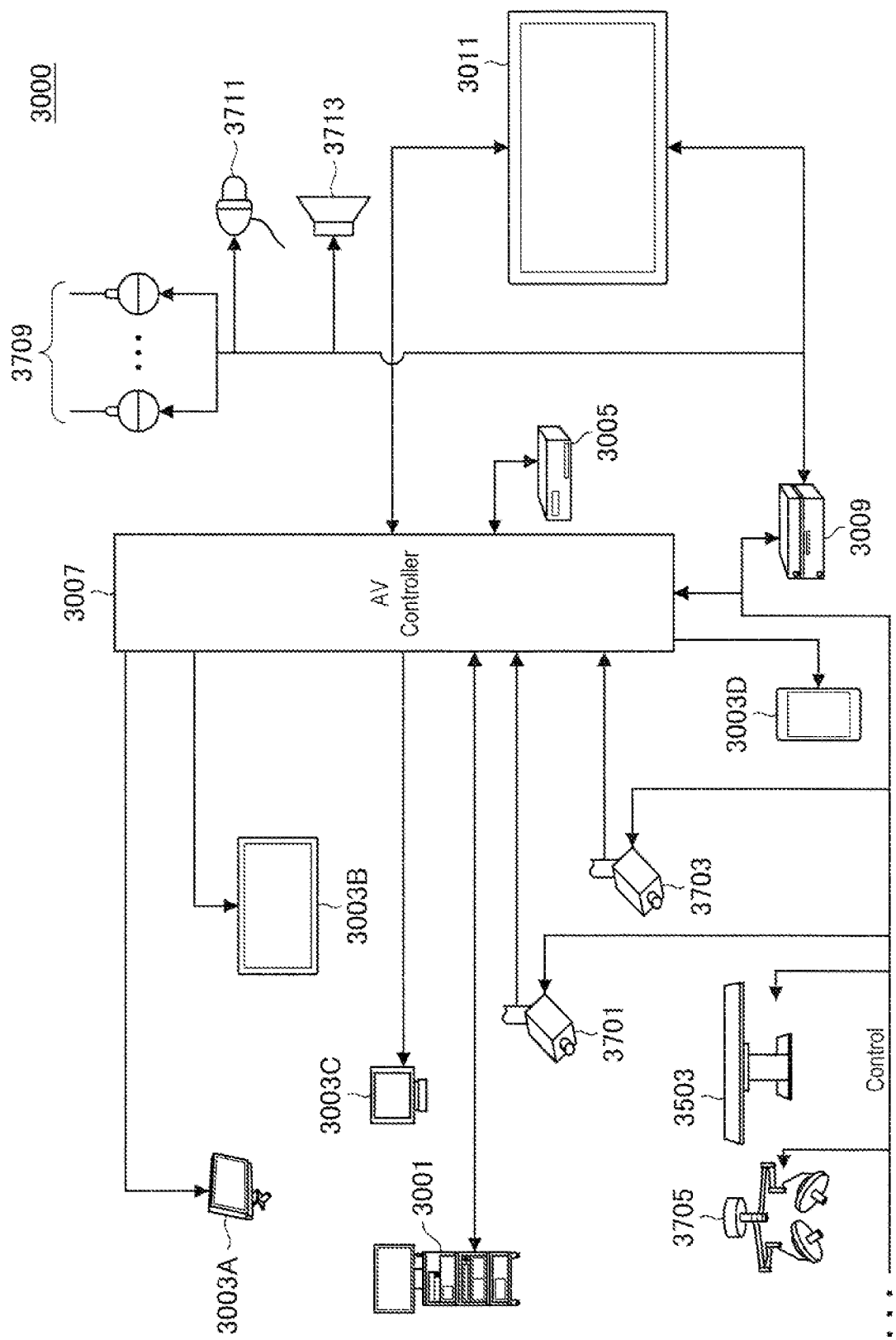
FIG. 1 is a diagram schematically illustrating an overall configuration of an operating room system according to an embodiment disclosed in the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that, in this description and the drawings, structural elements that have substantially the same function and structure are sometimes distinguished from each other using different alphabets after the same reference sign. However, when there is no need in particular to distinguish structural elements that have substantially the same function and structure, the same reference sign alone is attached.

Note that the description will be performed in the following order:

0. System Configuration Example
1. First Embodiment
1.1 Functional Configuration Example
1.2 Operation Example
1.3 Variation Examples
2. Second Embodiment
2.1 Functional Configuration Example
2.2 Variation Example
3. Conclusion

0. System Configuration Example

First, an example of a configuration of an operating room system according to an embodiment disclosed in this disclosure will be explained.

FIG. 1 is a diagram schematically illustrating an overall configuration of an operating-room system 3000 according to an embodiment disclosed in this disclosure. Referring to FIG. 1, the operating-room system 3000 is configured by a group of devices installed in an operating room being connected by an audio-visual controller (AV controller) 3007 and an operating room control device (simply referred to as a "control device") 3009 so as to be able to cooperate with each other.

Various devices can be installed in an operating room. As an example, FIG. 1 illustrates a group of devices 3001 of various kinds for endoscopic surgery, a ceiling camera 3701 provided on the ceiling of the operating room that captures images of the hands of a surgeon, a surgical field camera 3703 provided on the ceiling of the operating room that captures images of the overall state of the operating room, a plurality of display devices 3003A to 3003D, a recorder 3005, a patient bed 3503, lighting 3705, a microphone array (sound-collecting unit) 3709, an earphone 3711, and a directional speaker 3713.

Here, of these devices, the group of devices 3001 belongs to an endoscopic surgical system described later, and includes an endoscope and a display device that displays images captured by the endoscope. Each device belonging to the endoscopic surgical system is also called a medical device. On the other hand, the display devices 3003A to 3003D, the recorder 3005, the patient bed 3503, the lighting 3705, the microphone array (sound-collecting unit) 3709, the earphone 3711 and the directional speaker 3713 are devices that are provided in an operation room, for example, separately from the endoscopic surgical system. These devices not belonging to the endoscopic surgical system are called non-medical devices. The audio-visual controller 3007 and/or the operating-room-control device 3009 control the operation of these medical devices and non-medical devices in cooperation with each other.

The audio-visual controller 3007 comprehensively controls processing related to the image displays in the medical devices and non-medical devices. More specifically, of the devices included in the operating-room system 3000, the group of devices 3001, the ceiling camera 3701 and the surgical-field camera 3703 may be devices (hereinafter, also referred to as transmitting-source devices) having a function of transmitting information (hereinafter, also referred to as display information) to be displayed during surgery. In addition, the display devices 3003A to 3003D may be devices (hereinafter, also referred to as output-destination devices) to which display information is outputted. Moreover, the recorder 3005 may be a device that corresponds to being both a transmitting-source device and an output-destination device. The audio-visual controller 3007, together with controlling the operation of the transmitting-source devices and the output-destination devices and acquiring display information from the transmitting-source devices, has a function of transmitting the display information to the output-destination devices, and causing that information to be displayed or recorded. Note that, the display information is various images captured during surgery, and various information related to surgery, and the like (for example, body information of a patient, past examination results, surgery type, information indicating the operation room, information indicating the surgeon, information indicating surgical participants, and the like).

More specifically, information related to the image of an operation site in the body cavity of a patient captured by an endoscope may be transmitted as display information to the audio-visual controller 3007 from the group of devices 3001. In addition, information related to images of the hands of surgeon captured by the ceiling camera 3701 may be transmitted as display information from the ceiling camera 3701. Moreover, information related to images illustrating the overall state of an operation captured by the surgical field camera 3703 may be transmitted as display information from the surgical field camera 3703. Note that in the case where other devices having an imaging function are present in the operating-room system 3000, the audio-visual controller 3007 may acquire information related to images captured by the other devices as display information from the other devices.

Alternatively, for example, information of these images captured in the past may be recorded in the recorder 3005 by the audio-visual controller 3007. The audio-visual controller 3007 is able to acquire information of images captured in the past from the recorder 3005 as display information. Note that various information related to surgery may be recorded beforehand in the recorder 3005.

The audio-visual controller 3007 causes acquired display information (in other words, images captured during surgery, and various information related to surgery) to be displayed on at least any one of the display devices 3003A to 3003D as output-destination devices. In the example illustrated in FIG. 1, the display device 3003A is a display device located hanging from the ceiling of the operating room, the display device 3003B is a display device located on a wall surface of the operating room, display device 3003C is a display device located on a desk inside the operating room, and the display device 3003D is a mobile device (for example, a tablet PC (Personal Computer)) having a display function.

Moreover, although not illustrated in FIG. 1, the operating-room system 3000 may include devices that are outside the operating room. Devices outside of the operating room may be, for example, a server connected to a network constructed inside or outside a hospital, a PC used by the medical staff, a projector installed in a conference room of a hospital, and the like. In the case where such external devices are located outside of a hospital, the audio-visual controller 3007, in order to perform remote medical treatment, is able to cause display information to be displayed on a display device at another hospital via a television conference system or the like.

The operating-room-control device 3009 comprehensively controls processing other than processing related to image displays on non-medical devices. For example, the operating-room-control device 3009 controls driving of the patient bed 3503, the ceiling camera 3701, the surgical field camera 3703, the lighting 3705, the microphone array (sound-collecting unit) 3709, the earphone 3711, and the directional speaker 3713.

The operating-room system 3000 is provided with a centralized operation panel 3011, and a user, via the centralized operation panel 3011, is able to give instructions to the audio-visual controller 3007 for image displays, or is able to give instructions to the operating-room-control device 3009 for operation of non-medical devices. The centralized operation panel 3011 is configured by providing a touch panel on the display surface of the display device.

Figure 2:
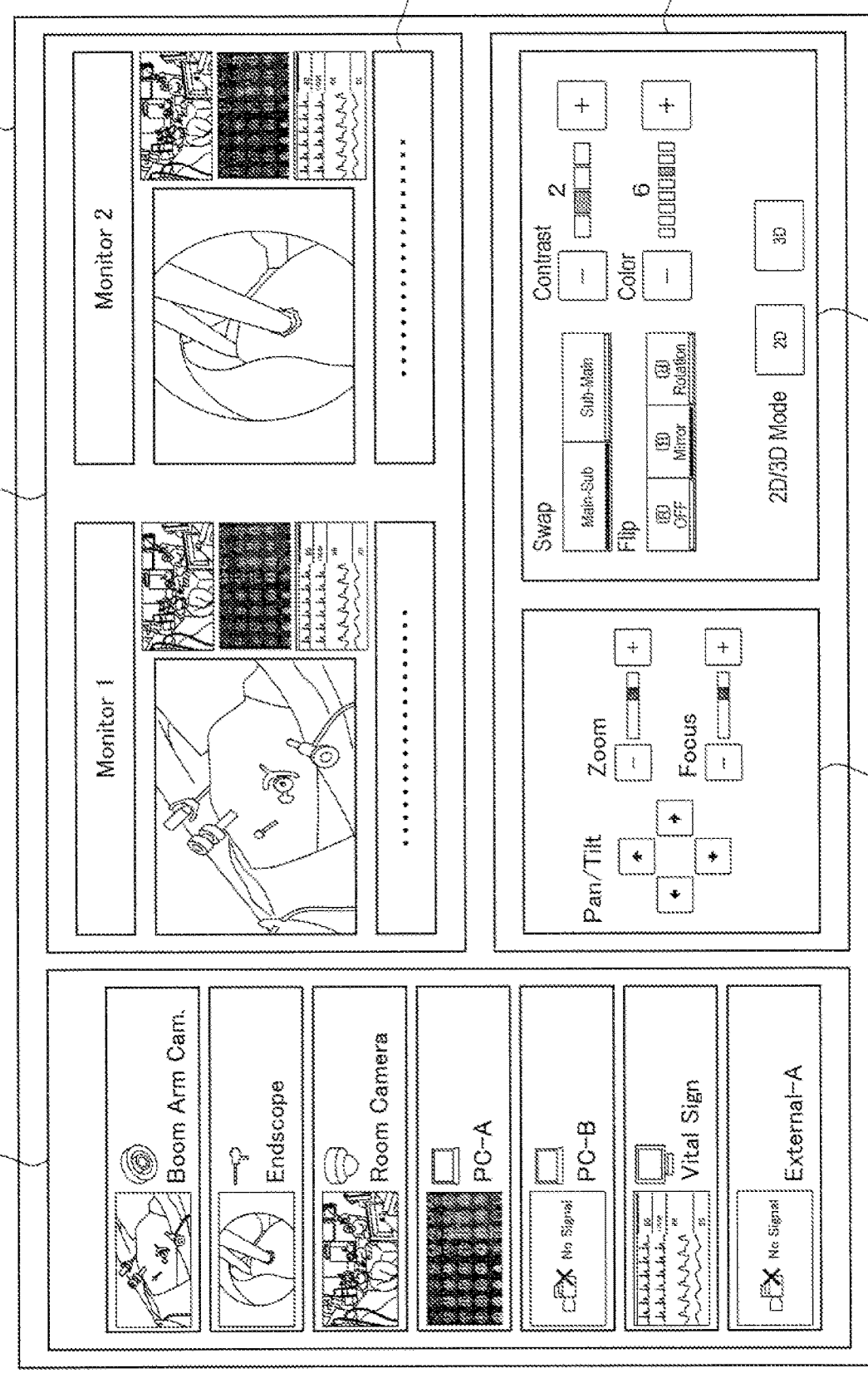
FIG. 2 is a diagram illustrating an example of an operation screen display on a centralized operation panel.

FIG. 2 is a diagram illustrating an example of an operation screen display on a centralized operation panel 3011. FIG. 2 illustrates an example of an operation screen that corresponds to the case in which two display devices are provided in the operating-room system 3000 as output-destination devices. Referring to FIG. 2, an operation screen 3800 is provided with a transmitting-source-selection area 3810, a preview area 3820 and a control area 3830.

In the transmitting-source-selection area 3810, transmitting-source devices included in the operating-room system 3000, and thumbnail screens representing display information that these transmitting-source devices have are correlated and displayed. A user is able to select desired display information to be displayed on a display device from among any one of the transmitting-source devices displayed in the transmitting-source-selection area 3810.

In the preview area 3820, previews are displayed of the screens to be displayed on the two display devices (Monitor 1 and Monitor 2) that are output-destination devices. In the example in FIG. 2, four images are PinP displayed on one display device. The four images are images corresponding to display information transmitted from the transmitting-source device selected in the transmitting-source-selection area 3810. Of the four images, one image is displayed relatively large as a main image, and the remaining three images are displayed relatively small as sub images. A user can exchange the main image and sub images by appropriately selecting the areas where the four images are displayed. In addition, a status-display area 3821 may be provided in a lower portion of the area where the four images are displayed, and status related to surgery (for example, the elapsed time of surgery, body information of the patient, and the like) may be appropriately displayed in that area.

The control area 3830 is provided with a transmitting-source-operation area 3831 in which GUI (Graphical User Interface) components for performing operation of transmitting-source devices are displayed, and an output-destination-operation area 3833 in which GUI components for performing operation of output-destination devices are displayed. In the example illustrated in FIG. 2, the transmitting-source-operation area 3831 is provided with GUI components for performing various operations (pan, tilt, and zoom) of a camera of a transmitting-source device having an imaging function. By appropriately selecting these GUI components, a user is able to control the operation of a camera of a transmitting-source device. Note that even though omitted in FIG. 2, in the case where the transmitting-source device selected in the transmitting-source-selection area 3810 is a recorder (in other words, in the case where images recorded in the past by the recorder are displayed in the preview area 3820), the transmitting-source-selection area 3831 may be provided with GUI components for performing operations such as play, stop, rewind, fast forward and the like of the images.

In addition, the output-destination-operation area 3833 is provided with GUI components for performing various operations (swap, flip, color adjustment, contrast adjustment, switching between a 2D display and 3D display) of a display on a display device that is an output-destination device. By appropriately selecting these GUI components, a user is able to operate a display on a display device.

Note that the operation screen that is displayed on the centralized operation panel 3011 is not limited to the example illustrated in FIG. 2, and a user, via the centralized operation panel 3011, can input operations to each of the devices included in the operating-room system 3000 and controlled by the audio-visual controller 3007 and operating-room-control device 3009.

An example of configuration of the operating-room system 3000 according to an embodiment disclosed in the disclosure has been explained above. Here, during surgery, it is common for voice communication to be performed among surgical participants. However, there may be factors present that interfere with voice communication. For example, in cases such as where surgical participants are wearing masks, or the like, the masks may become a factor interfering with voice communication. Moreover, noise that is generated by devices used in surgery may become a factor interfering with voice communication.

In addition, outputting speech collected by microphones attached to surgical participants may also be presumed. However, surgical participants (for example, surgeons, assistants, and the like) need to keep clean, and microphones that are difficult to clean must be kept clean, so outputting speech collected by microphones attached to surgical participants is not realistic. Therefore, it is preferred that a technique be provided that is capable of ensuring more reliable voice communication during surgery among surgical participants. Note that in the following explanation, voice (voice or speech) and sound will be distinguished from each other.

1. First Embodiment

Continuing, a first embodiment according to the disclosure will be explained.

[1.1 Functional Configuration Example]

Figure 3:
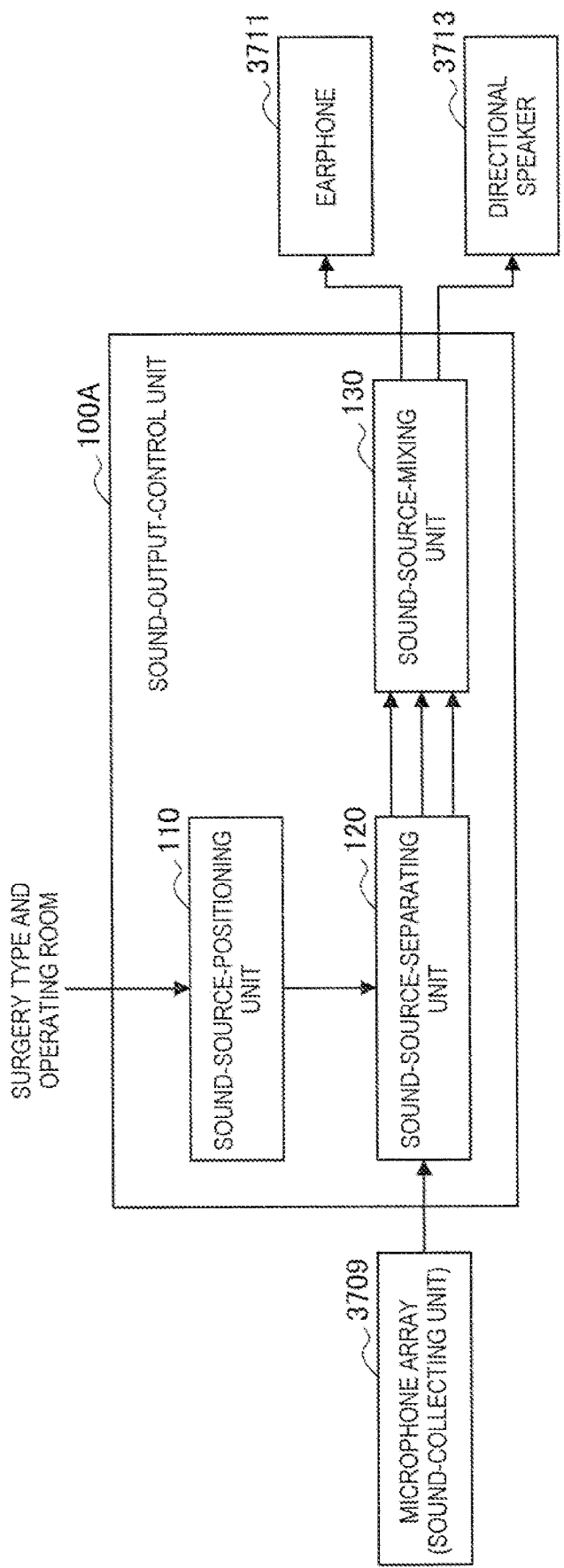
FIG. 3 is a diagram illustrating an example of a configuration of a sound-output-control unit according to a first embodiment disclosed in this disclosure.

First, an example of a configuration of a sound-output-control unit 100A according to this first embodiment disclosed in the disclosure will be explained. FIG. 3 is a diagram illustrating an example of a configuration of a sound-output-control unit 100A according to a first embodiment disclosed in the disclosure. The sound-output-control unit 100A may be included in the above-described operating-room-control device 3009, or may be included in a control device different than the operating-room control device 3009. As illustrated in FIG. 3, the sound-output-control unit 100A according to a first embodiment disclosed in the disclosure includes a sound-source-positioning unit 110, a sound-source-separating unit 120, and a sound-source-mixing unit 130.

Note that in this first embodiment according to the disclosure, the case is presumed in which the function of the sound-output-control unit 100A is achieved by executing a program that is read from a storage device (for example, a magnetic storage device, a semiconductor storage device, and optical storage device, a magneto-optical storage device, or the like) by an arithmetic operation device, however, the function of the sound-output-control unit 100A may also be achieved by dedicated hardware (dedicated electronic circuit).

The sound-output-control unit 100A controls sound output by a sound-output device on the basis of information related to surgery. With this configuration, it is possible to ensure more reliable voice communication during surgery among surgical participants. Hereinafter, an earphone 3711 and a directional speaker 3713 will be explained as examples of sound-output devices, however, the form of sound-output devices is not limited to these. Various kinds of information are presumed as information related to surgery, however, first, the case in which information related to surgery includes sound-source-position information in an operating room will be explained. In addition, the case in which the sound-output-control unit 100A controls sound output based on sound information collected by a microphone (sound-collecting unit) 3709 will be presumed.

Figure 4:
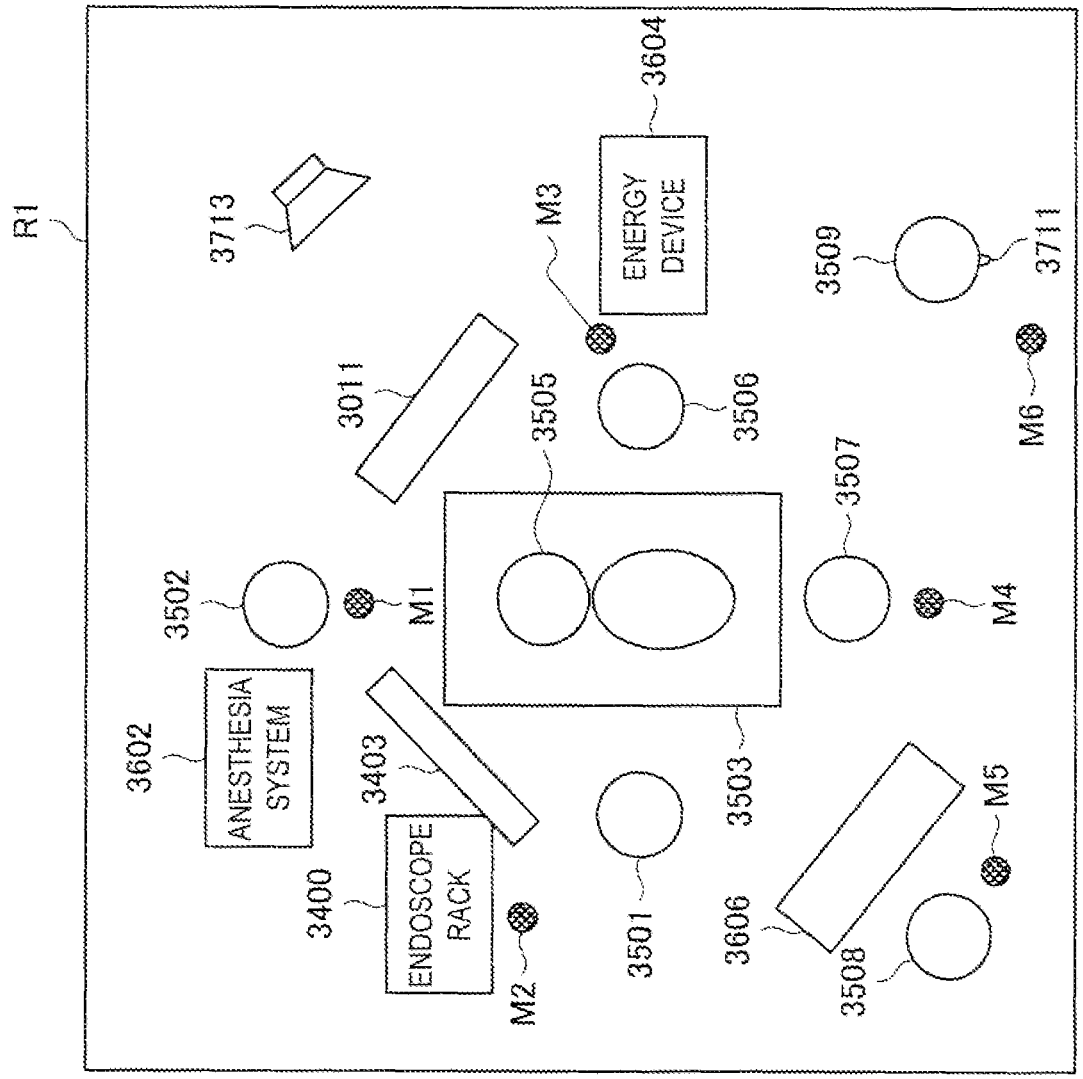
FIG. 4 is a view of the state of an operating room as seen from above.

FIG. 4 is a view of the state of an operating room R1 as seen from above. As illustrated in FIG. 4, there is a patient bed 3503 present in the operating room R1, and a patient 3505 is lying on the patient bed 305. In addition, as examples of surgical participants there are present a surgeon 3501, an anesthesiologist 3502, an assistant 3506, a circulating nurse 3509, a scrub nurse 3508, and an endoscopist 3507. There is a possibility that these surgical participants will emit sound (may become sound sources) during surgery. It should be noted that surgical participants are not limited to these.

Moreover, in the operating room R1 there are present as examples of devices, an endoscope rack 3400, an anesthesia system 3602 and an energy device 3604. There is a possibility that these devices may also emit sounds (may become sound sources) during surgery. It should be noted that devices are not limited to these. In addition, there are microphones M1 to M6 present in the operating room R1. The microphones M1 to M6 may constitute a microphone array (sound-collecting unit) 3709. The number of microphones is not particularly limited.

In addition, it is presumed that the circulating nurse 3509 will move around during surgery however, controlling the directional speaker 3713 to match the movement of the circulating nurse 3509 is difficult. Therefore, sound output to the circulating nurse 3509 is performed by an earphone 3711 that is worn by the circulating nurse 3509. In other words, the sound-output-control unit 100A controls sound output by the earphone (sound-output device) 3711 associated with the circulating muse 3509.

On the other hand, it is presumed that the other surgical participants do not move much during surgery, so sound output to the other surgical participants is performed by using the directivity of the directional speaker 3713. In other words, the sound-output-control unit 100A controls sound output according to the positions of those other surgical participants (claim 6). More specifically, the sound-output-control unit 100A controls sound output by the directional speaker (sound-output device) 3713 so that sound is outputted toward the positions of the other surgical participants. However, which surgical participants wear an earphone 3711 is not limited.

In addition, the centralized operation panel 3011 described above is present in the operating room R1, and a display device 3403 is also present. An image of the surgical site inside the body cavity of the patient that is captured by the endoscope is displayed on the display device 3403. The surgeon 3501 performs surgery on the patient using various instruments while viewing in real-time images of the surgical site that is displayed on the display device 3403. Moreover, an instrument table 3606 is present in the operating room R1. Various instruments are placed on the instrument table 3606, and the scrub muse 3508 performs work of taking the various instruments from the instrument table 3606 and handing them to surgeon 3501 or the like.

Returning to FIG. 3, the explanation will be continued. The sound-output-control unit 100A, by the sound-source-positioning unit 110, determines the sound-source position based on predetermined data. Determination of the sound-source-position information may be performed in any manner. For example, it is possible to decide the sound-source position according to at least any one of the surgery type, the operating room, and the surgical participants (for example, the surgeon). Therefore, the sound-output-control unit 100A, by the sound-source-positioning unit 110, determines the sound-source-position information based on at least any one of the surgery type, operating room, and the surgical participants. Hereinafter, an example will be explained in which the sound-source-position information is determined based on the surgery type and the operating room.

First, the sound-output-control unit 100A, by the sound-source-positioning unit 110, acquires information indicating the surgery type and operating room. Information indicating the surgery type and operating room may be acquired in any manner. For example, in the case where information indicating the surgery type and operating room is recorded in the recorder 3005, the information indicating the surgery type and the operating room may be acquired from the recorder 3005. Alternatively, information indicating the surgery type and the operating room may be inputted via the centralized operation panel 3011. The sound-output-control unit 100A, by the sound-source-positioning unit 110, determines the sound-source-position information on the basis of information indicating the surgery type and the operating room.

Figure 5:
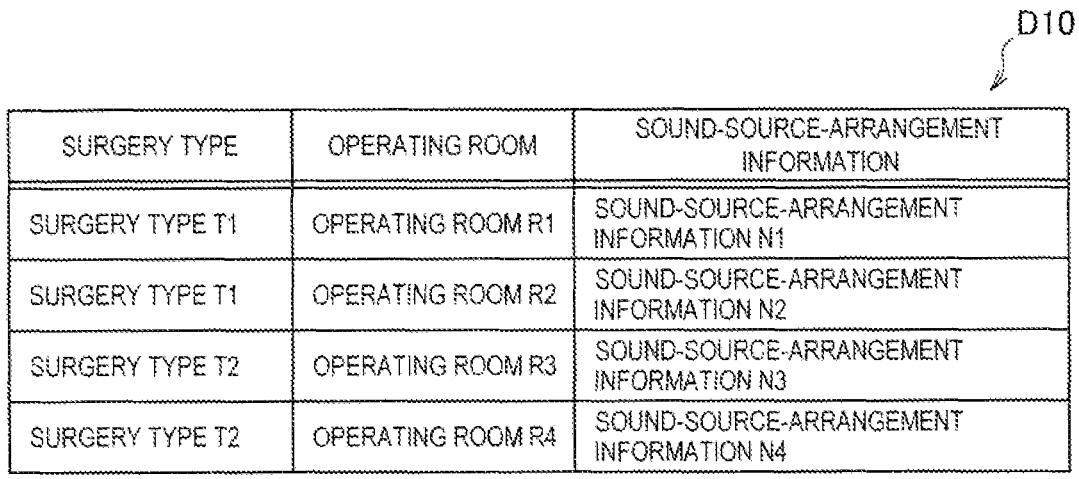
FIG. 5 is a diagram illustrating an example of a configuration of a correlation database in which information indicating a surgery type and operating room is correlated with sound-source-arrangement information.

FIG. 5 is a diagram illustrating an example of a configuration of a correlation database D10 in which information indicating a surgery type and operating room is correlated with sound-source-arrangement information. For example, data that correlates the surgery type T1, operating room R1 and sound-source-arrangement information N1 is included in the correlation database D10. The contents of the correlation database D10 may be appropriately updated so as to fit the hospital where the correlation database D10 is used. Note that the correlation database D10 may be recorded anywhere. For example, the correlation database D10 may be recorded in the recorder 3005.

Figure 6:
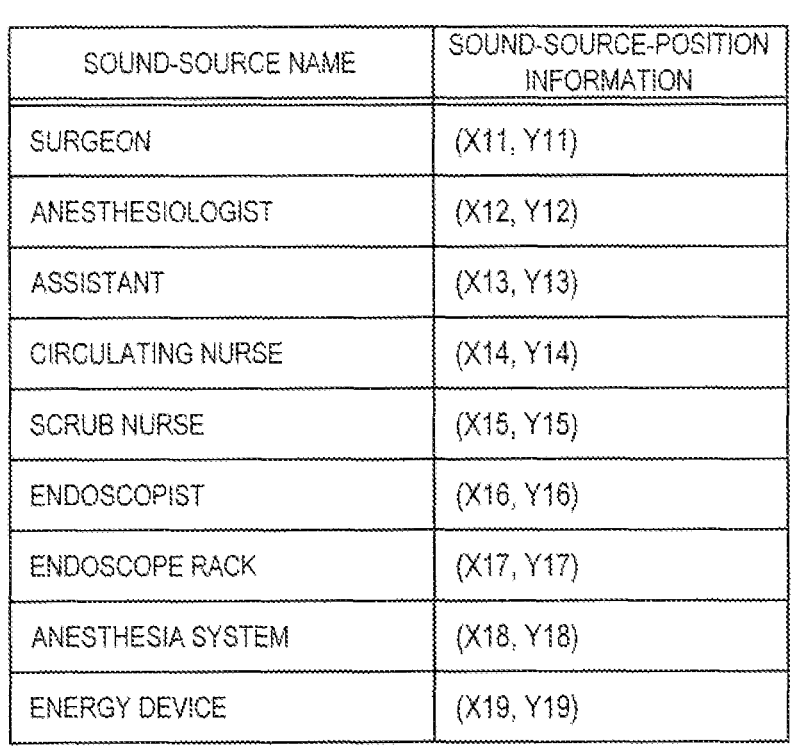
FIG. 6 is a diagram illustrating an example of a configuration of sound-source-arrangement information.

FIG. 6 is a diagram illustrating an example of a configuration of sound-source-arrangement information N1. As illustrated in FIG. 6, the sound-source-arrangement information N1 includes a plurality of combinations of sound-source names (sound-source-identification information) and sound-source-position information. Note that in FIG. 6, sound-source-position information is expressed in two-dimensional coordinates as an example, however, the form for expressing the sound-source-position information is not limited, and may also be expressed in three-dimensional coordinates. In addition, the sound-source-arrangement information N1 may be recorded anywhere. For example, the sound-source-arrangement information N1 may be recorded in the recorder 3005.

For example, the sound-output-control unit 100A, by the sound-source-positioning unit 110, acquires a combination of correlated sound-source-arrangement information that matches a combination of acquired information indicating the surgery type and operating room. Here, the case is presumed in which the combination of correlated sound-source-arrangement information N1 matches a combination of surgery type T1 and operating room R1. For example, sound-source-position information (X11, Y11) of a sound source "surgeon" is included in the sound-source-arrangement information N1.

Note that sound-source-position information obtained in this way may not correctly represent the actual sound-source position. Therefore, the sound-source-position information may be made recognizable by a predetermined surgical participant. For example, in the case where the sound-source-position information is displayed on the centralized operation panel 3011, and it is confirmed that the displayed sound-source-position information correctly expresses the actual sound-source position, a predetermined surgical participant may enter the fact that the sound-source-position information is correct. Then, after entering the fact that the sound-source-position information is correct, subsequent operation may be executed.

FIG. 7 is a diagram illustrating an example of a configuration of a microphone-arrangement database D20. As illustrated in FIG. 7, data that correlates the microphone ID and the microphone position is included in the microphone-arrangement database D20. Note that in FIG. 7, the microphone position is expressed by two-dimensional coordinates as an example, however the form for expressing the microphone position is not limited and may be expressed by three-dimensional coordinates. In addition, the microphone-arrangement database D20 may be recorded anywhere. For example, the microphone-arrangement database D20 may be recorded in the recorder 3005.

FIG. 8 is a diagram illustrating an example of a configuration of a sound-output-device database P1. As illustrated in FIG. 8, data that correlates the surgical participants and the sound-output device is included in the sound-output-device database P1. For example, the sound-output device "earphone" is correlated with the surgical participant "circulating nurse". Note that the sound-output-device database P1 may be recorded anywhere. For example, the sound-output-device database P1 may be recorded in the recorder 3005.

Returning to FIG. 3, the explanation will be continued. The sound-output-control unit 100A, by the sound-source-separating unit 120 performs sound separation of the sound information collected by the microphones M1 to M6 on the basis of the positions (X21, Y21) to (X26, Y26) of the microphones M1 to M6 and the sound-source-position information (X11, Y11) to (X19, Y19). As a result of sound separation, sound information separated for each sound source is obtained.

In sound-source separation, the attributes of the surgical participants (for example, gender, age, and the like) are further taken into consideration. In other words, in sound-source separation, voice frequencies corresponding to the attributes of the surgical participants may be further taken into consideration. In that case, it is expected that the accuracy of sound-source separation will be improved. Then, the sound-output-control unit 100A, by the sound-source-mixing nit 130 controls the sound output on the basis of the results of sound separation.

For example, the sound-output-control unit 100A, by the sound-source-mixing unit 130, on the basis of the results of sound-source separation, reduces noise from sound information collected by the microphones M1 to M6, then controls the sound output on the basis of sound information after noise reduction. For example, there is a possibility that devices (endoscope rack 3400, anesthesia system 3602 and energy device 3604) will emit noise. Therefore, the sound-output-control unit 100A, by the sound-source-mixing unit 130, reduces noise by mixing sound information from the surgical participants (surgeon 3501, anesthesiologist 3502, assistant 3506, circulating nurse 3509, scrub nurse 3508, and endoscopist 3507), and controls sound output on the basis of sound information after noise reduction.

Note that as described above, the sound-output-control unit 100A, by the sound-source-mixing unit 130, controls sound output by an earphone (sound-output device) 3711 correlated with the circulating nurse 3509. In addition, the sound-output-control unit 100A, by the sound-source-mixing unit 130, controls sound output according to the positions of the other surgical participants. More specifically, the sound-output-control unit 100A controls sound output by the directional speaker 3713 so that sound is outputted toward the positions of the other surgical participants.

[1.2 Operation Example]

An example of a configuration of the sound-output-control unit 100A according to a first embodiment disclosed in this disclosure is explained above with reference to FIG. 1 to FIG. 8. Continuing, an example of operation of the sound-output-control unit 100A according to a first embodiment disclosed in this disclosure will be explained.

Figure 9:
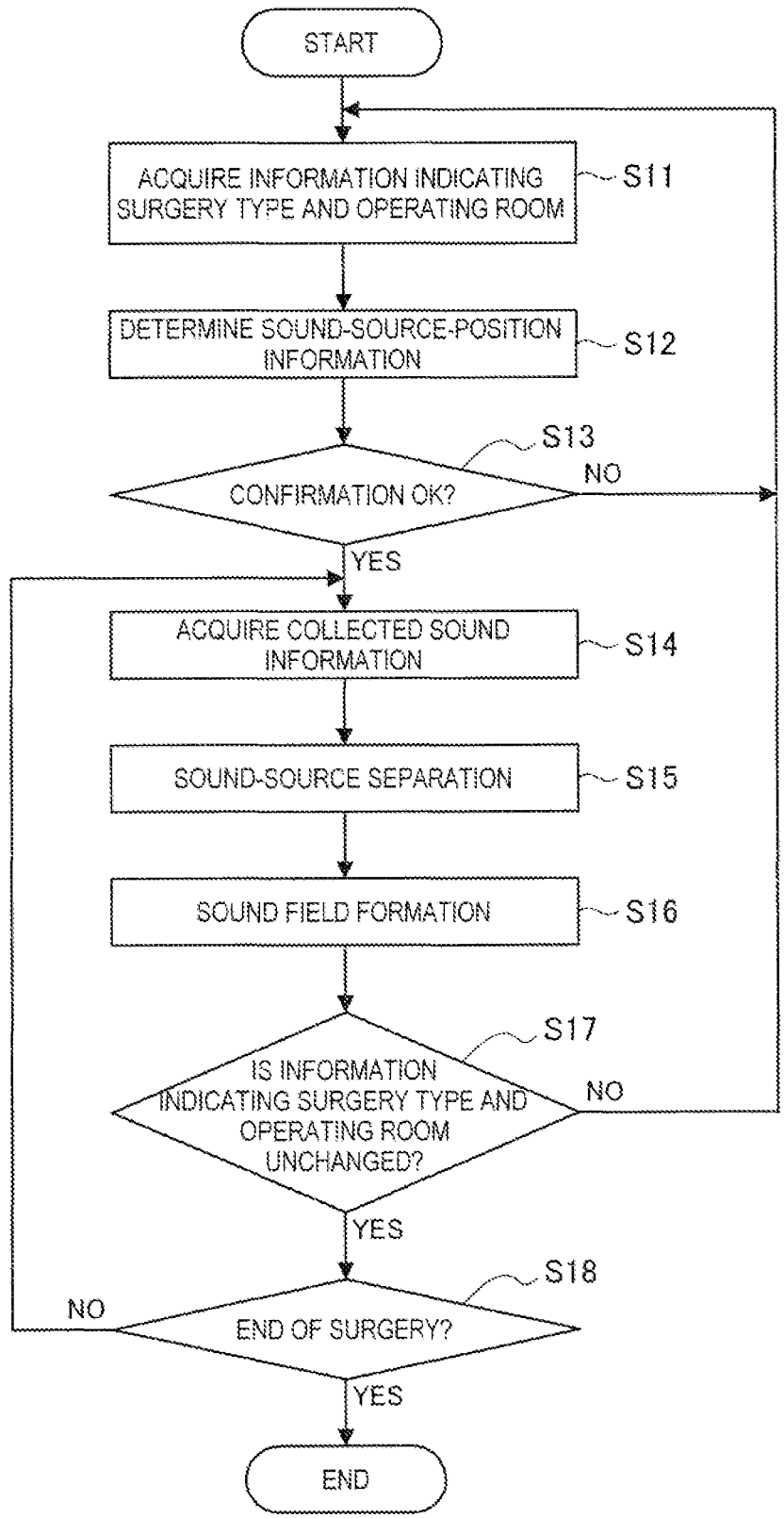
FIG. 9 is a flowchart illustrating an example of an operation of a sound-output-control unit according to a first embodiment disclosed in this disclosure.

FIG. 9 is a flowchart illustrating an example of an operation of a sound-output-control unit 100A according to a first embodiment disclosed in this disclosure. As illustrated in FIG. 9, first, the sound-output-control unit 100A, by the sound-source-positioning unit 110, acquires information indicating a surgery type and operating room (S11). Then, the sound-source-positioning unit 110 determines the sound-source position on the basis of the acquired information indicating a surgery type and operating room (S12). The determined sound-source-position information is displayed on the centralized operation panel 3011.

Continuing, in the case where it is not confirmed that the displayed sound-source-position information correctly expresses the actual sound-source position (S13: NO), operation moves to S11. On the other hand, in the case where it is confirmed that the displayed sound-source-position information correctly expresses the actual sound-source position (S13: YES), the sound-output-control unit 100A, by the sound-source-separating unit 120, acquires sound information collected by the microphones M1 to M6 (S14).

Next, the sound-output-control unit 100A, by the sound-source-separating unit 120, performs sound separation of sound information collected by the microphones M1 to M6 on the basis of the positions (X21, Y21) to (X26, Y26) of the microphones M1 to M6 and the sound-source-position information (X11, Y11) to (X19, Y19) (S15). Continuing, the sound-output-control unit 100A, by the sound-source-mixing unit 130, reduces noise from sound information collected by the microphones M1 to M6 on the basis of the results of sound-source separation, and controls sound output on the basis of sound information after noise reduction. As a result a sound field with reduced noise is formed (S16).

Continuing, in the case where there is change in information indicating the surgery type and operating room (S17: NO), the sound-output-control unit 100A moves operation to SI. On the other hand, in the case where there is no change in information indicating the surgery type and operating room (S17: YES), the sound-output-control unit 100A moves operation to S18. In the case where surgery is not finished (S18: NO), the sound-output-control unit 100A moves operation to S14, however, in the case where surgery is finished (S18: YES), the sound-output-control unit 100A ends the voice output operation.

Note that the end of surgery may be determined in any manner. For example, in the case where microscopic surgery or endoscopic surgery is performed, the end of imaging of the surgical field may be regarded as the end of surgery. Alternatively, in the case where procedures to be performed in surgery are set in the preoperative plan, the point in time when all of the procedures to be performed in surgery have been detected may be regarded as the end of surgery, or the point in time when the last procedure to be performed in surgery has been detected may be regarded as the end of surgery. Alternatively, a point in time at which a predetermined amount of time has elapsed from these points in time may be regarded as the end of surgery.

[1.3 Variation Examples]

Various variations may be applied to the first embodiment according to this disclosure. For example, in the description above, an example of determining sound-source-position information is explained, however, the sound-source-position information may be determined in any manner. For example, the sound-output-control unit 100A, by the sound-source-positioning unit 110, may determine the sound-source-position information on the basis of images captured by the surgical-field camera (imaging device) 3703. For determining the sound-source position, a three-dimensions measurement technique (SLAM: Simultaneous Localization and Mapping) and a recognition technique may be used.

In addition, in the case where surgical participants are wearing masks, in some cases face recognition of the surgical participants may be difficult. Therefore, in the case where surgical participants are made to wear a nametag, and the nametag is recognized from an image, the position of the nametag may be determined as the position of the surgical participant corresponding to that nametag. Moreover, in the case where markers are attached to devices, and the markers are recognized from images, the position of a marker may be determined as the position of the device to which the marker is attached. Note that, image detection is passive sensing that does not use radio waves, so is safely performed even during surgery.

In addition, sound sources such as surgical participants and devices are considered to emit a certain amount of heat. Therefore, the sound-output-control unit 100A, by the sound-source-positioning unit 110, may determine sound-source-position information on the basis of detection results by a thermography device. For example, in the case where a position of heat that is emitted beyond a certain amount is detected by a thermography device, that position may be determined as the position of a sound some. Note that heat detection is passive sensing that does not use radio waves, so is safely performed even during surgery.

Furthermore, by attaching a transmitter to sound sources such as surgical participants and devices, and installing a receiver in the operating room, the sound-output-control unit 100A, by the sound-source-positioning unit 110, may determine sound-source-position information on the basis of received results by the receiver of radio signals transmitted from the transmitters. For example, the position of a transmitter (in other words, the position of a sound source) may be determined on the basis of the direction of arrival of a radio signal to the receiver and the reception strength of the radio signal at the receiver.

Moreover, the sound-output-control unit 100A, by the sound-source-positioning unit 110, may intentionally cause a sound to be outputted from a sound source such as surgical participants and devices, determine sound-source position information on the basis of sound information collected by the microphones M1 to M6. When doing this, sound sources may be identified by causing different sounds to be emitted from each sound source, or the order of sound output from each sound source may be set beforehand, and sound sources may be identified on the basis of the order of collected sound.

These methods for determining the sound-source-position information may be used alone, or in order to improve the accuracy of determining sound-source-position information, any of these methods for determining sound-source-position information may be used in combination. Alternatively, the sound-source-position information does not need to be determined by the sound-source-positioning unit 110. For example, the sound-source-position information may be manually inputted via the centralized operation panel 3011 or the like.

Furthermore, in the description above, an example is explained in which on the basis of the results of sound-source separation, the sound-output-control unit 100A, by the sound-source-mixing unit 130, reduces noise from sound information collected by the microphones M1 to M6, and controls sound output on the basis of sound information after noise reduction. However, processing based on the results of sound-source separation is not limited to noise reduction. For example, processing based on the results of sound-source separation may be processing that relatively emphasizes sound information from predetermined sound sources.

In other words, the sound-output-control unit 100A, by the sound-source-mixing unit 130, may relatively emphasize sound information from a predetermined sound source on the basis of results of sound-source separation of sound information based on sound collected by the microphones M1 to M6, and control sound output on the basis of the sound information after emphasis. Relative emphasis of sound information from a predetermined sound source may be an increase in volume of sound information from a predetermined sound source, or may be a decrease in volume of sound information from a predetermined sound source (including eliminating the volume of the sound), or may be both.

The predetermined sound source may be a predetermined surgical participant, or may be a predetermined device. For example, of the sound information based on sound collected by the microphones M1 to M6, the sound-output-control unit 100A may relatively emphasize sound information from a predetermined surgical participant (for example, a surgeon, or the like), and control sound output on the basis of the sound information after emphasis. The predetermined surgical participant may be set beforehand.

In addition, determining from which surgical participant the sound information will be relatively emphasized may differ according to the surgical participants that will listen to the output sound. For example, in the case where the scrub nurse will listen to the output sound, the sound information from the surgeon and assistant may be relatively emphasized.

Alternatively, in the case where another surgical participant is detected according to the line of sight of one surgical participant (the case where another surgical participants is detected in the direction of the line of sight of one surgical participant), sound information from the other surgical participant may be relatively emphasized in the output sound that the one surgical participant will listen to. Moreover, in order to facilitate the exchange of speech between the two surgical participants in the case of such detection, sound information of the two surgical participants may both be emphasized.

In addition, of the sound information based on sound collected by the microphones M1 to M6, the sound-output-control unit 100A may relatively emphasize sound information from a predetermined device and control sound output on the basis of the sound information after emphasis. The predetermined device may be set in advance or may be decided in accordance with stages of surgery. For example, in the case of performing cataract surgery, turbidity of the lens is removed by an ultrasonic aspiration device. When the lens is crushed by the ultrasonic aspiration device, a high pitch is emitted and the surgeon performs surgery while checking this high pitch.

Therefore, in the case where a sound having a higher frequency than a predetermined threshold value is emitted, the sound-output-control unit 100A may relatively emphasize sound information of the sound information based on sound collected by the microphones M1 to M6 that is from the ultrasonic aspiration device, and control sound output on the basis of sound information after emphasis. On the other hand, in the case where sound having an lower frequency than a predetermined threshold value is emitted, the sound-output-control unit 100A may relatively emphasize sound information of the sound information based on sound collected by the microphones M1 to M6 that is from another sound source, and control sound output on the basis of sound information after emphasis, or may not have to emphasize the sound information.

Moreover, in the description above, an example is explained in which sound-source separation is performed of sound information collected by the microphones M1 to M6. However, sound-source separation does not need to be performed. For example, the sound-output-control unit 100A may specify a microphone from the microphones M1 to M6 on the basis of a predetermined sound source (for example, specify the closest microphone to a predetermined sound source), and control the sound output based on sound information collected by the specified microphone.

The predetermined sound source may be a predetermined surgical participant, or may be a predetermined device. For example, the sound-output-control unit 100A may specify a microphone on the basis of a predetermined surgical participant (for example, specify the microphone closest to the predetermined surgical participant), and on the basis of sound information collected by the specified microphone, control sound output according to that surgical participant. The predetermined surgical participant may be set beforehand.

Moreover, determining which microphone to specify may differ depending on the surgical participants that will listen to the output sound. For example, in the case where the scrub nurse will listen to the output sound, a microphone may be specified on the basis of the surgeon and assistant (the microphone closest to the surgeon and the microphone closest to the assistant may be specified).

Alternatively, in the case where another surgical participant is detected according to the line of sight of one surgical participant (case where another surgical participant is detected in the direction of the line of sight of one surgical participant), a microphone that collects sound that will be listened to by the one surgical participant may be specified on the basis of the other surgical participant (the microphone closest to the other surgical participant may be specified). In addition, in order to facilitate the exchange of speech between the two surgical participants in the case of such detection, the microphone that collects sound that will be listened to by the other surgical participant may be specified on the basis of the one surgical participant (the microphone closest to the one surgical participant my be specified).

A first embodiment according to this disclosure is explained above.

2. Second Embodiment

Continuing, a second embodiment according to this disclosure will be explained.

[2.1 Functional Configuration Example]

Figure 10:
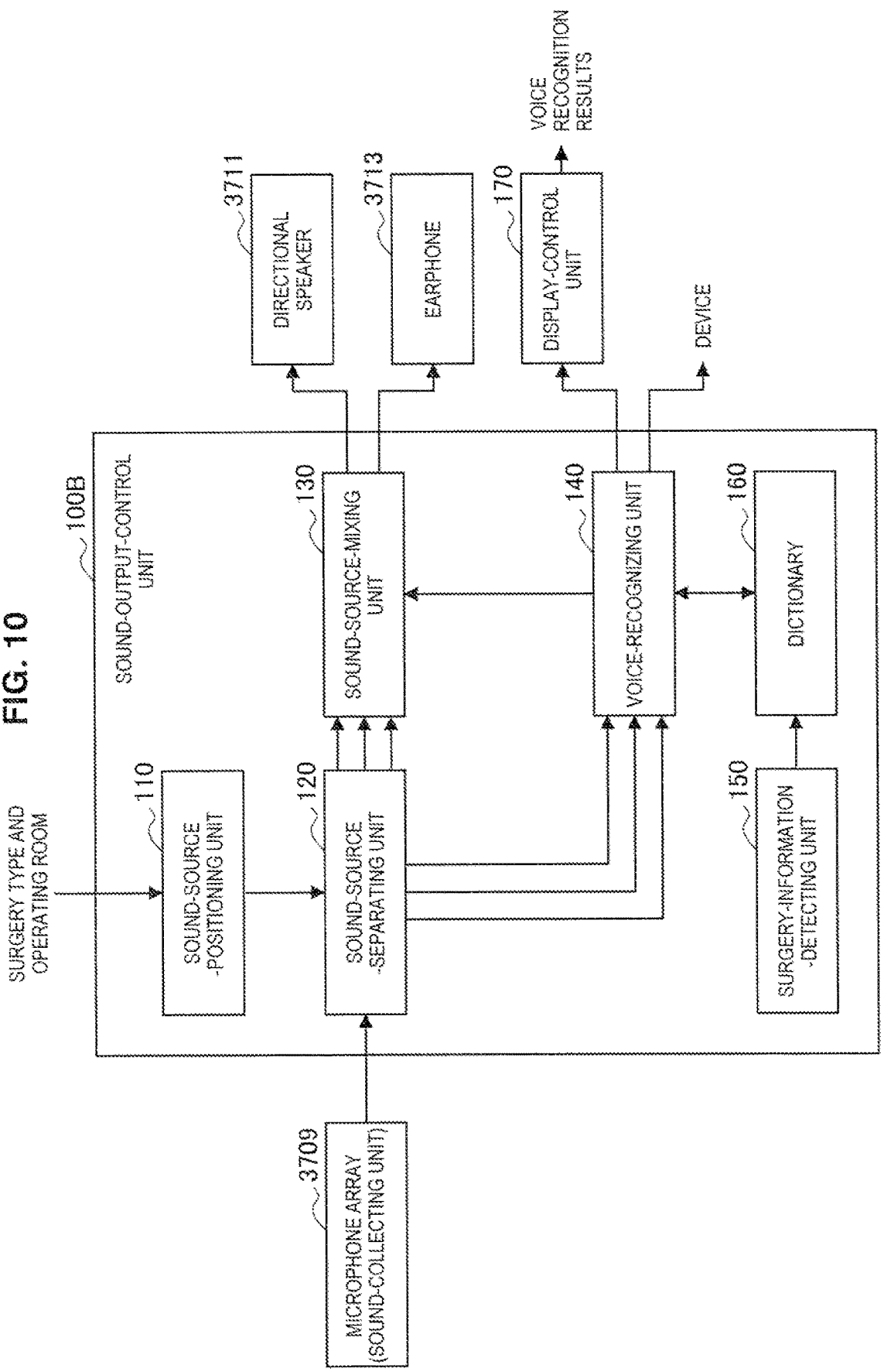
FIG. 10 is a diagram illustrating an example of a configuration of a sound-output-control unit and a display-control unit according to a second embodiment disclosed in this disclosure.

First, an example of a configuration of a sound-output-control unit 100B and a display-control unit 170 according to a second embodiment disclosed in this disclosure will be explained. FIG. 10 is a diagram illustrating an example of a configuration of a sound-output-control unit 100B and a display-control unit 170 according to a second embodiment disclosed in this disclosure. The sound-output-control unit 100B may be included in the operating-room-control device 3009 described above, or may be included in a control device different from the operating-room control device 3009. In addition, the display-control unit 170 may be included in the audio-visual controller 3007 described above, or may be included in a control device different from the audio-visual controller 3007 (the same control device as or different control device from the control device in which the sound-output-control unit 100B is included).

As illustrated in FIG. 10, in the sound-output-control unit 100B according to this second embodiment disclosed in this disclosure, the point of including a voice-recognizing unit 140, a surgery-information-detecting unit 150, and a dictionary 160 in addition to a sound-source-positioning unit 110, a sound-source-separating unit 120 and a sound-source-mixing unit 130 differs from the sound-output-control unit 100A according to the first embodiment disclosed in this disclosure. Hereinafter, the voice-recognizing unit 140, the surgery-information-detecting unit 150 and the dictionary 160 will mainly be explained.

First, as devices become more sophisticated, the necessity of calling navigation functions and annotation functions, controlling parameters used in the devices, and the like is increasing, and the operation of devices is also becoming more complicated. Therefore, there is an increasing demand for a technique that enables operation of devices by voice command without touching the device. However, in some cases, sound that is inputted directly into a device may include sound other than a voice command, and in such a case, there is a possibility that accuracy of recognizing a voice command by a device may not be improved. Therefore, voice recognition results based on sound information from a predetermined surgical participant may be outputted to the device.

In other words, the sound-output-control unit 100B, by the voice-recognizing unit 140, acquires sound information that has been separated for each sound source from the sound-source-separating unit 120 as the result of sound-source separation, and performs voice recognition based on sound information from a predetermined surgical participant. Then, the sound-output-control unit 100B, by the voice-recognizing unit 140, controls output of voice recognition based on sound information from the predetermined surgical participant to the device. With this kind of configuration, accuracy of recognition of voice commands by a device is improved.

Note that in order to input voice recognition results to a device, sound directly inputted to the device may be excluded from being a target of command recognition. The predetermined surgical participant may be anyone as long as the person is capable of inputting a voice command to the device, and may be a surgeon, or may be an anesthesiologist. In addition, a device that is capable of receiving voice commands is not particularly limited, and in the example described above, the device may be the endoscope rack 3400, or may be the anesthesia system 3602, or may be the energy device 3604.

In addition, in the case where predetermined information is in speech emitted from a certain surgical participant (hereinafter, referred to as a "first surgical participant"), there is a possibility that the speech is speech intended for a specified surgical participant (hereinafter, referred to as a "second surgical participant"). As an example, in the case where the name of the second surgical participant is included in speech emitted from the first surgical participant, there is a possibility that the speech is speech intended for the second surgical participant. As another example, in the case where a predetermined keyword that is used in exchange with the second surgical participant is included in speech emitted from the first surgical participant, there is a possibility that the speech is speech intended for the second surgical participant.

Therefore, in the case where predetermined information related to the 30 second surgical participant is included in voice recognition results based on sound information from the first surgical participant, the sound-output-control unit 100B may relatively emphasize sound information from the first surgical participant and control sound output according to the second surgical participant on the basis of sound information after the emphasis (may control sound output toward the second surgical participant). At this time, in order to facilitate the exchange of speech between the two surgical participants, sound information between the two surgical participants may both be emphasized.

Moreover, by controlling the sound output as described above, sound information from surgical participants becomes easy to listen to, however, sound information from surgical participants may also be made to be more reliably grasped. For example, the display-control unit 170 may control the display of voice recognition results based on sound information from a predetermined surgical participant. The voice recognition results may be displayed anywhere. For example, the voice recognition results may be displayed on the centralized operation panel 3011.

FIG. 11 is a diagram illustrating an example of a display of voice-recognition results. As illustrated in FIG. 11, voice recognition results may be displayed as a history T0 that includes past voice recognition results. Moreover, as illustrated in FIG. 11, in addition to past voice recognition results, the time when voice recognition was performed (for example, as illustrated in FIG. 11, with the current time as a reference, the amount of time to the time when voice recognition was performed) and the surgical participant who emitted the speech may be displayed in the history T0.

In addition, a dictionary 160 for voice recognition is generally used in voice recognition. Test data and speech are con-elated and recorded in the dictionary 160, and by comparing sound information collected by the microphones M1 to M6 with the speech recorded in the dictionary 160, text data that is correlated with speech matching sound information collected by the microphones M1 to M6 is extracted from the dictionary 160.

At this time, in the case where the progress of a procedure or surgery being performed by a surgeon is detected by the surgery-information-detecting unit 150, in order to improve accuracy of voice recognition, the sound-output-control unit 100B, by the voice-recognizing unit 140, may select a dictionary 160 to be used in voice recognition on the basis of the progress of a procedure or surgery being performed by the surgeon. For example, in the case where a procedure in which the use of a predetermined device is highly probable, a dictionary 160 having high accuracy of recognition of commands that can be received by that device may be selected. In addition, in the case where surgical instruments to be used differ according to the process of the surgery, a dictionary 160 having high accuracy of recognition of surgical instruments to be used during that progress may be selected.

Note that, progress of a procedure or surgery being performed by a surgeon may be detected in any manner. For example, progress of a procedure or surgery being performed by a surgeon may be detected on the basis of images captured by a the ceiling camera 3701 that is provided on the ceiling of the operating room and that captures the hands of the surgeon. Alternatively, progress of a procedure or surgery being performed by a surgeon may be detected on the basis of sound information collected by the microphones M1 to M6.

[2.2 Variation Examples]

Various variation examples can be applied to this second embodiment according to this disclosure. For example, in the description above, an example is explained in which sound-source separation of sound information collected by the microphones M1 to M6 is performed. However, sound-source separation does not need to be performed. For example, the sound-output-control unit 100B may specify a microphone from among the microphones M1 to M6 on the basis of a predetermined sound source (for example, specify the microphone closest to the sound source), and control output of voice-recognition results based on sound information collected from the specified microphone to a device.

In addition, in the case where predetermined information related to the second surgical participant is included in the voice recognition results based on sound information from the first surgical participant, the sound-output-control unit 100B may specify a microphone on the basis of the first surgical participant (for example, specify the microphone closest to the first surgical participant), and control sound output to the second surgical participant that is based on sound information collected from the specified microphone. At this time, in order to facilitate the exchange of speech between the two surgical participants, the microphone that collects sound listened to by the first surgical participant may be specified on the basis of the second surgical participant (the microphone closest to the second surgical participant may be specified).

Moreover, in order to more surely grasp sound information from surgical participants, the display-control unit 170 may control the display of voice recognition results based on sound information collected by a microphone specified by the sound-output-control unit 100B. The voice recognition results may be displayed anywhere. For example, the voice recognition results may be displayed on the centralized operation panel 3011.

Furthermore, similar to the first embodiment according to this disclosure, in the case where surgery ends, the voice output operation may be ended. Here, the end of surgery may be determined in any manner. For example, in the case where text data (for example, text data such as "surgery has ended" or the like) indicating the end of surgery is included in the voice recognition results, detection of the text data indicating the end of surgery may be regarded as the end of surgery.

A second embodiment according to this disclosure has been explained above.

3. Conclusion

As was explained above, with the embodiments according to this disclosure, a control device 3009 is provided that includes a sound-output-control unit 100A that controls sound output by a sound-output device on the basis of information related to surgery. With this configuration, it is possible to ensure more reliable voice communication among surgical participants during surgery. Since it is easier for surgical participants to communicate with each other, smooth surgery is achieved, and the time of surgery is shortened. In addition, mistakes due to miscommunication of instructions among surgical participants and transmission leakage of instructions are reduced.

Moreover, since surgical participants do not have to interact with each other in a loud voice, the burden and stress placed on the surgical participants is reduced. Furthermore, since surgical participants do not have to interact with each other in a loud voice, feelings of anxiety and stress given to persons other than surgical participants (for example, a patient, and the like) are also reduced. In addition, by collecting the speech of surgical participants with a non-contact microphone array microphones do not need to be attached to surgical participants, so management of cleanliness becomes easier.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
A control device, including:
a sound-output-control unit that controls sound output by a sound-out device on a basis of information related to surgery.

(2)
The control device according to (1),
in which the information related to surgery includes sound-source-position information of an operating room.

(3)
The control device according to (2),
in which the sound-output-control unit determines the sound-source-position information on a basis of predetermined data.

(4)
The control device according to (3),
in which the sound-output-control unit determines the sound-source-position information on a basis of at least any one of a surgery type, an operating room, or a surgical participant.

(5)
The control device according to (3),
in which the sound-output-control unit determines the sound-source-position information on a basis of at least any one of an image captured by an imaging device, a reception result of a wireless signal transmitted from a transmitter, a detection result by a thermography device, or sound information collected by a sound-collecting unit.

(6)
The control device according to any one of (1) to (5),
in which the sound-output-control unit controls sound output by a sound output device correlated with a surgical participant, or controls sound output according to a position of a surgical participant.

(7)
The control device according to any one of (1) to (6),
in which the sound-output-control unit controls sound output based on sound information collected by a sound-collecting unit.

(8)
The control device according to (7),
in which the sound collecting unit includes a plurality of microphones; and the sound-output-control unit controls sound output based on the sound information collected by the plurality of microphones.

(9)
The control device according to (8),
in which the sound-output-control unit controls sound output on a basis of a result of sound-source separation of the sound information based on positions of the plurality of microphones and the sound-source-position information.

(10)
The control device according to (9),
in which the sound-output-control unit reduces noise from the sound information on a basis of a result of sound-source separation of the sound information based on sound collected by the sound-collecting unit, and controls sound output on a basis of sound information after noise reduction.

(11)
The control device according to (9) or (10),
in which the sound-output-control unit relatively emphasizes sound information from a predetermined sound source on a basis of a result of sound-source separation of the sound information based on sound collected by the sound-collecting unit, and controls sound output on a basis of the sound information after emphasis.

(12)
The control device according to (11),
in which the sound-output-control unit relatively emphasizes sound information from a predetermined surgical participant among sound information based on sound collected by the sound-collecting unit, and controls sound output on a basis of the sound information after emphasis.

(13)
The control device according to (11),
in which the sound-output-control unit relatively emphasizes sound information from a predetermined device among sound information based on sound collected by the sound-collecting unit, and controls sound output on a basis of the sound information after emphasis.

(14)
The control device according to any one of (9) to (13),
in which the sound-output-control unit controls output to a device of a voice recognition result based on sound information from a predetermined surgical participant.

(15)
The control device according to any one of (9) to (14),
in which, in a case where predetermined information related to a second surgical participant is included in a voice recognition result based on sound information from a first surgical participant, the sound-output-control unit relatively emphasizes sound information from the first surgical participant, and controls sound output according to the second surgical participant on a basis of the sound information after emphasis.

(16)
The control device according to any one of (9) to (15), including:
a display-control unit that controls a display of a voice recognition result based on sound information from a predetermined surgical participant.

(17)

The control device according to any one of (13) to (16),
in which the sound-output-control unit selects a dictionary to be used in voice recognition on a basis of progress of a procedure or surgery being performed by a surgeon.

(18)

The control device according to (8),
in which the sound-output-control unit specifies a microphone on a basis of a predetermined sound source, and controls sound output based on sound information collected by the specified microphone.

(19)

The control device according to (18),
in which the sound-output-control unit specifies a microphone on a basis of a predetermined surgical participant, and controls sound output according to the surgical participant on a basis of sound information collected by the specified microphone.

(20)

The control device according to (18) or (19),
in which the sound-output-control unit controls output to a device of a voice recognition result based on sound information collected by a specified microphone.

(21)

The control device according to any one of (18) to (20),
in which, in a case where predetermined information related to a second surgical participant is included in a voice recognition result based on sound information from a first surgical participant, the sound-output-control unit specifies a microphone on a basis of the first surgical participant, and controls sound output based on sound information collected by the specified microphone.

(22)

The control device according to (18) or (21), including:
a display-control unit that controls a display of a voice recognition result based on sound information collected by a specified microphone.

(23)

A control method including:
controlling, by a processor, sound output by a sound-output device on a basis of information related to surgery.

(24)

A program for causing a computer to function as a control device including:
a sound-output-control unit that controls sound output by a sound-output device on a basis of information related to surgery.

(25)

A sound-output system, including:
a sound-output device that performs sound output; and
a control device including
a sound-output-control unit that controls sound output by the sound-output device on a basis of information related to surgery.

REFERENCE SIGNS LIST 100A, 100B sound-output-control unit
110 sound-source-positioning unit
120 sound-source-separating unit
130 sound-source-mixing unit
140 voice-recognizing unit
150 surgery-information-detecting unit
160 dictionary
170 display-control unit
3000 operating-room system (sound-output system)
3005 recorder
3007 audio-visual controller
3009 operating-room control device (control device)
3400 endoscope rack (device)
3602 anesthesia system (device)
3604 energy device (device)
3701 ceiling camera
3703 surgical field camera
3709 microphone (sound-collecting unit)
3711 earphone (sound-output device)
3713 directional speaker (sound-output device)

The invention claimed is:

1. An apparatus for controlling sound output from surgical participants in an operating room, comprising:
a sound-output controller comprising circuitry configured to:
receive surgical information identifying an operating room;
acquire sound information collected by a plurality of microphones located in the identified operating room;
receive sound-source information identifying locations of surgical participants and locations of the plurality of microphones in the identified operating room;
separate the acquired sound information into separate sound components based on the locations of the surgical participants and the locations of the plurality of microphones in the identified operating room, in the received sound-source information, wherein each sound component corresponds to sound information produced by a different sound source;
remove one or more sounds components from the separated sound components; and
provide sound information based on a mix of the remaining sound components to one or more sound output devices located in the identified operating room.

2. The control device according to claim 1,
wherein the sound-source information is based on predetermined data.

3. The control device according to claim 2,
wherein the sound-source information is based on at least any one of an image captured by an imaging device, a reception result of a wireless signal transmitted from a transmitter, a detection result by a thermography device, or sound information collected by the plurality of microphones.

4. The control device according to claim 1,
wherein the circuitry of the sound-output controller is further configured to control sound output by at least one of a sound output device correlated with a surgical participant or according to a position of a surgical participant.

5. The control device according to claim 1,
wherein the circuitry of the sound-output controller is further configured to reduce noise from the separated sound components.

6. The control device according to claim 1,
wherein the circuitry of the sound-output controller is further configured to:
emphasize one or more separated sound components relative to one or more other separated sound components; and
provide sound information to the one or more sound output devices with the one or more separated sound components emphasized relative to the one or more other separated sound components.

7. The control device according to claim 6,
wherein the circuitry of the sound-output controller is further configured to increase the volume of one or more separated sound components.

8. The control device according to claim 1,
wherein the circuitry of the sound-output controller is further configured to perform voice recognition based on a separated sound component corresponding to a predetermined surgical participant.

9. The control device according to claim 8,
wherein, in a case where a result of the voice recognition result based on a separated sound component from a first surgical participant includes sound information from a second surgical participant, the circuitry of the sound-output controller is further configured to emphasize sound information from the first surgical participant relative to the sound information from the second surgical participant.

10. The control device according to claim 8, further comprising:
a display controller that controls a display of a voice recognition result based on the separated sound component corresponding to the predetermined surgical participant.

11. The control device according to claim 8,
wherein the circuitry of the sound-output controller is further configured to select a dictionary to be used in voice recognition on a basis of progress of a procedure or surgery being performed by a surgeon.

12. The control device according to claim 1,
wherein the circuitry of the sound-output controller is further configured to:
specify a microphone among the plurality of microphones on a basis of a predetermined sound source; and
provide sound information based on sound information collected by the specified microphone.

13. The control device according to claim 12,
wherein the circuitry of the sound-output controller is further configured to:
specify a microphone among the plurality of microphones on a basis of a predetermined surgical participant; and
provide sound information according to the surgical participant on a basis of sound information collected by the specified microphone.

14. The control device according to claim 12,
wherein the circuitry of the sound-output controller is further configured to produce sound information based on a result of voice recognition based on sound information collected by the specified microphone.

15. The control device according to claim 12,
wherein, in a case where a result of the voice recognition based on a separated sound component from a first surgical participant includes sound information from a second surgical participant, the circuitry of the sound-output controller is further configured to specify a microphone on a basis of the first surgical participant and provide sound information based on sound information collected by the specified microphone.

16. The control device according to claim 12, further comprising:
a display controller that controls a display of a voice recognition result based on sound information collected by the specified microphone.

17. A method for controlling sound output from surgical participants in an operating room, comprising:
receiving surgical information identifying an operating room;
acquiring sound information collected by a plurality of microphones located in the identified operating room;
receiving sound-source information identifying locations of surgical participants and locations of the plurality of microphones in the identified operating room;
separating the acquired sound information into separate sound components based on the locations of the surgical participants and the locations of the plurality of microphones in the identified operating room, in the received sound-source information, wherein each sound component corresponds to sound information produced by a different sound source;
removing one or more sounds components from the separated sound components; and
providing sound information based on a mix of the remaining sound components to one or more sound output devices located in the identified operating room.

18. A computer readable medium readable by a processor for causing a computer to control sound output from surgical participants in an operating room, the computer readable medium configured to:
receive surgical information identifying an operating room;
acquire sound information collected by a plurality of microphones located in the identified operating room;
receive sound-source information identifying locations of surgical participants and locations of the plurality of microphones in the identified operating room;
separate the acquired sound information into separate sound components based on the locations of the surgical participants and the locations of the plurality of microphones in the identified operating room, in the received sound-source information, wherein each sound component corresponds to sound information produced by a different sound source;
remove one or more sounds components from the separated sound components; and
provide sound information based on a mix of the remaining sound components to one or more sound output devices located in the identified operating room.

19. A sound-output system for controlling sound output from surgical participants in an operating room, comprising:
a plurality of microphones that collect sound information in the operating room;
a sound-output device that performs sound output in the operating room; and
a sound-output controller comprising circuitry configured to:
receive surgical information identifying an operating room;
acquire sound information collected by the plurality of microphones located in the identified operating room;
receive sound-source information identifying locations of surgical participants and locations of the plurality of microphones in the identified operating room;
separate the acquired sound information into separate sound components based on the locations of the surgical participants and the locations of the plurality of microphones in the identified operating room, in the received sound-source information, wherein each sound component corresponds to sound information produced by a different sound source;
remove one or more sounds components from the separated sound components; and provide sound information based on a mix of the remaining sound components to the sound-output device located in the identified operating room.

\* \* \* \* \*